United States Patent

Natsch

(10) Patent No.: US 9,192,559 B2
(45) Date of Patent: Nov. 24, 2015

(54) COMPOSITIONS

(75) Inventor: Andreas Natsch, Uetikon (CH)

(73) Assignee: Givaudan SA, Vernier (CH)

( * ) Notice: Subject to any disclaimer, the term of this patent is extended or adjusted under 35 U.S.C. 154(b) by 787 days.

(21) Appl. No.: 12/518,680

(22) PCT Filed: Dec. 11, 2007

(86) PCT No.: PCT/CH2007/000627
§ 371 (c)(1),
(2), (4) Date: Jul. 7, 2010

(87) PCT Pub. No.: WO2008/071027
PCT Pub. Date: Jun. 19, 2008

(65) Prior Publication Data
US 2010/0284942 A1    Nov. 11, 2010

(30) Foreign Application Priority Data
Dec. 15, 2006   (GB) .................................. 0625069.0

(51) Int. Cl.
| | | |
|---|---|---|
| *A61K 8/33* | (2006.01) | |
| *A61K 8/49* | (2006.01) | |
| *A61K 8/92* | (2006.01) | |
| *A61K 8/02* | (2006.01) | |
| *A61K 31/11* | (2006.01) | |
| *A01N 35/04* | (2006.01) | |
| *A61Q 5/02* | (2006.01) | |
| *A61Q 15/00* | (2006.01) | |
| *A61Q 13/00* | (2006.01) | |
| *A61Q 19/00* | (2006.01) | |
| *A01P 3/00* | (2006.01) | |
| *A61Q 19/10* | (2006.01) | |
| *A61K 8/34* | (2006.01) | |

(52) U.S. Cl.
CPC .............. *A61K 8/4973* (2013.01); *A01N 35/04* (2013.01); *A61K 8/33* (2013.01); *A61K 8/345* (2013.01); *A61K 8/347* (2013.01); *A61Q 19/00* (2013.01); *A61K 2800/524* (2013.01)

(58) Field of Classification Search
CPC .............................. A61K 8/4973; A01N 35/04
See application file for complete search history.

(56) References Cited

U.S. PATENT DOCUMENTS

| | | | |
|---|---|---|---|
| 5,630,847 A | 5/1997 | Roetker | |
| 5,891,422 A | 4/1999 | Pan et al. | |
| 6,174,521 B1 | 1/2001 | Li et al. | |
| 7,060,289 B2 * | 6/2006 | Wassenaar | 424/443 |
| 2002/0098211 A1 | 7/2002 | Cupferman | |
| 2003/0211057 A1 * | 11/2003 | Majeti et al. | 424/59 |
| 2004/0101505 A1 * | 5/2004 | Payne et al. | 424/70.31 |
| 2005/0222276 A1 | 10/2005 | Schmaus et al. | |
| 2005/0228032 A1 | 10/2005 | Merianos et al. | |
| 2006/0057175 A1 * | 3/2006 | Ciccognani et al. | 424/405 |
| 2006/0257352 A1 * | 11/2006 | Saar | 424/74 |

FOREIGN PATENT DOCUMENTS

| | | |
|---|---|---|
| CN | 1330917 A | 1/2002 |
| DE | 3501426 A1 | 7/1985 |
| DE | 19927891 A1 | 12/2000 |
| DE | 10042710 A1 | 3/2002 |
| DE | 10206759 A1 | 8/2003 |
| DE | 102004031210 A1 | 2/2006 |
| EP | 0570794 A2 | 11/1993 |
| EP | 1000542 A1 | 5/2000 |
| EP | 1206933 A1 | 5/2002 |
| EP | 1537781 A | 6/2005 |
| EP | 1537781 A1 | 6/2005 |
| EP | 1543829 A1 | 6/2005 |
| EP | 1543830 A1 | 6/2005 |
| FR | 2866234 A1 | 8/2005 |

(Continued)

OTHER PUBLICATIONS

Esposito, L. J. et al., Kirk-Othmer Encyclopedia of Chemical Technology, "Vanillin", 1997.*
Taku et al. JPH072640, published: Jan. 6, 1995, English Machine Translataion obtained on May 8, 2015.*
English Language Abstract for JP2003081736 taken from esp@cenet.com.
English Language Abstract for DE10042710 taken from esp@cenet.com.
English Language Abstract for JP2003192581 taken from esp@cenet.com.

(Continued)

*Primary Examiner* — Johann R Richter
*Assistant Examiner* — Genevieve S Alley
(74) *Attorney, Agent, or Firm* — Norris McLaughlin & Marcus PA

(57) ABSTRACT

There are provided personal care products and compositions that comprise at least one diol compound selected from the group consisting of 1,2-pentanediol, 1,2-hexanediol, 1,2-octanediol, 2-methyl-1,3-propandiol, and 3-(2-ethyl-hexyloxy)-1,2-propandiol in a total concentration of 0.1% to 0.5% (w/w); and at least one preservative enhancer compound selected from the group consisting of benzaldehyde, 4-methylbenzaldehyde, heliotropine, vanilline, 4-hydroxybenzaldehyde, 3-hydroxybenzaldehyde, 4-methoxybenzaldehyde and 3-methoxybenzaldehyde, 2,4-dihydroxybenzaldehyde, 3-hydroxy-4-methoxybenzaldehyde, 3,5-dihydroxybenzaldehyde, and 4-hydroxy-2-methoxybenzaldehyde, in a total concentration of 0.05 to 0.5% (w/w), in a cosmetically acceptable base. The composition optionally contains at least one compound selected from the group consisting of phenoxyethanol, 2-phenylethanol, and benzylalcohol, in a total concentration of 0.05 to 0.3% (w/w), but does not contain other classic bactericidal, fungicidal, sporicidal or preservative compounds. The invention is further directed to methods of forming such compositions and products and the use of preservatives and preservative enhancers in such compositions and products.

20 Claims, No Drawings

(56) References Cited

FOREIGN PATENT DOCUMENTS

| | | | |
|---|---|---|---|
| GB | 2152817 A | 8/1995 |
| JP | H072640 * | 1/1995 |
| JP | H03190815 A | 8/1997 |
| JP | H1053510 A | 2/1998 |
| JP | 11310506 A | 11/1999 |
| JP | 11322591 A | 11/1999 |
| JP | 2001302475 A | 10/2001 |
| JP | 2003081736 A | 3/2003 |
| JP | 2003192581 A | 7/2003 |
| JP | 2004067626 A | 3/2004 |
| JP | 2004182639 A | 7/2004 |
| JP | 2005015360 A | 1/2005 |
| JP | 2005068095 A | 3/2005 |
| JP | 2005232012 A | 9/2005 |
| JP | 2005526036 A | 9/2005 |
| JP | 2006519192 A | 8/2006 |
| WO | 9734972 A1 | 9/1997 |
| WO | 9817756 A1 | 4/1998 |
| WO | 0065011 A1 | 11/2000 |
| WO | 0213776 A2 | 2/2002 |
| WO | 03034994 A2 | 5/2003 |
| WO | 2005102276 A | 11/2005 |
| WO | 2005123028 A1 | 12/2005 |
| WO | 2006082151 A1 | 8/2006 |
| WO | 2006119981 A1 | 11/2006 |
| WO | 2007071089 A | 6/2007 |
| WO | 2007071090 A | 6/2007 |

OTHER PUBLICATIONS

English Language Abstract for DE10206759 taken from esp@cenet.com.

B.L. Bowles, et al., "Antibotulinal Properties of Selected Aromatic and Aliphatic Aldehydes", Journal of Food Protection, vol. 56, No. 9, pp. 788-794, 1993.

A. Lopez-Malo, et al., "Mixtures of Natural and Synthetic Antifungal Agents", Advances in Experimental Medicine and Biology, vol. 571, pp. 261-306, 2006.

* cited by examiner

COMPOSITIONS

This is an application filed under 35 USC 371 of PCT/CH2007/000627.

The present invention relates to preserved personal care product compositions and their use in personal care products applied to the human skin or scalp, and methods of making such products.

Preservatives are used in personal care products (products applied to the skin or scalp either to remain there or to be rinsed off) to preserve these products against microbial spoilage and to extend their shelf life.

Antimicrobial compounds used for product preservation may fall into one or more of the following classes based on the effect they have on the microorganism, in particular bacteria and fungi. A germistatic compound inhibits the growth of germs, while a germicidal compound kills germs. An antibacterial or antifungal may inhibit growth of the microorganisms or kill them or both. Many antimicrobial compounds are not effective against fungal spores. A bacteriostatic compound inhibits growth of bacteria, while a bactericide kills bacteria (reduces their number). Similarly, a fungistatic compound inhibits the growth of fungi (molds and yeast), while a fungicide kills fungi (reduces their number). A sporicide kills spores of fungi or bacteria. Spores, especially endospores, are formed by some bacteria to survive during periods of deprivation and are significantly more difficult to kill. Fungi form spores for reproduction and these spores are significantly more difficult to kill than the vegetative form of the fungi.

A broad band preservative effect including a bactericidal and fungicidal activity was previously only partially attained in personal care products, or attained only by addition of certain fungicides, in particular formaldehyde, formaldehyde donors, halogenated compounds, compounds belonging to the class of parabens and a variety of specific fungicides.

Combinations of certain different 1,2-alkanediols or 1,2-alkanediols with certain well known preservatives, in particular phenoxyethanol or parabens are known from DE10206759, Beilfuss et al. in SOFW-Journal 131, 11-2005, p. 30-36, WO2005/102276, WO2006/045746, EP 1537781, and EP 0524548.

Notably, none of the above prior art documents disclose a combination of 1,2-alkanediols with benzaldehydes or benzaldehyde derivatives.

The following classic antimicrobial and in particular fungicide compounds commonly find use in personal care products.

Formaldehyde donors include in particular diazolidinyl urea (CAS 78491-02-8), imidazolidinyl urea (CAS 39236-46-9), and DMDM Hydantoin (CAS 6440-58-0).

Halogenated compounds include in particular 2,4-dichlorobenzyl-alcohol (CAS 1777-82-8), Chloroxylenol (also known as 4-chloro-3,5-dimethyl-phenol, CAS 88-04-0), Bronopol (also known as 2-bromo-2-nitropropane-1,3-diol, CAS 52-51-7), iodopropynyl butyl carbamate (CAS 55406-53-6).

Paraben compounds include in particular Methyl-paraben (CAS 99-76-3), Ethyl-paraben (CAS 120-47-8), Propyl-paraben (CAS 94-13-3), Butyl-paraben (CAS 94-26-8), Isopropyl-paraben (CAS 4191-73-5), and Benzyl-paraben (CAS 94-18-8).

Other fungicides include Quaternium-15 (CAS 51229-78-8), methyl-chloroisothiazolinone (CAS 26172-55-4), and methylisothiazolinone (CAS 2682-20-4).

There are concerns that some of these fungicide compounds may constitute health hazards, for example, iodopropynyl butyl carbamate, formaldehyde and formaldehyde donors, methyl-chloroisothiazolinone (CAS 26172-55-4), and methylisothiazolinone are considered highly allergenic/sensitizing.

Accordingly there is an interest in replacing the abovementioned compounds in personal care products applied to human skin or scalp while maintaining a good broad band preservative activity including a sporicidal effect.

Various milder preservatives are known but they do not provide a sufficient preservative effect, for example p-hydroxy-benzoic acid, methyl-paraben, ethyl-paraben, propyl-paraben, isopropyl-paraben, butyl-paraben, isobutyl-paraben, and benzyl-paraben. Further, phenoxyethanol, 2-phenylethanol, and benzyl alcohol are mild to the skin and do not raise similar safety concerns as do the preservatives mentioned above.

However, these compounds on their own are able to provide a sufficient bactericidal activity only at a high concentration and even at a high concentration do not have a sufficient sporicidal effect.

Applicant has now identified a composition of diol compounds according to formula I as shown herein below that, in combination with benzaldehyde and certain benzaldehyde derivative compounds of formula II as shown herein below, provide a preservative action in personal care products and provide a broad band preservative activity including a sporicidal effect. This is important for the stability and shelf life of the product.

The chemical structures of the diol compounds useful in compositions and personal care products according to the invention are shown below in formula I herein below.

They consist of the following diols: 1,2-pentanediol, 1,2-hexanediol, 1,2-octanediol, 2-methyl-1,3-propandiol, and 3-(2-ethyl-hexyloxy)-1,2-propandiol. The structure of these compounds is shown below.

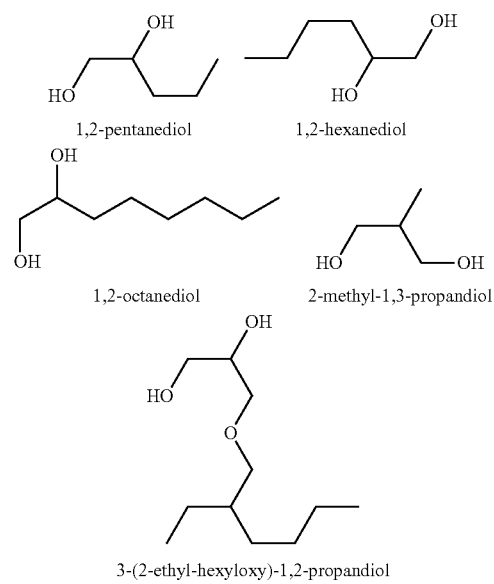

The benzaldehyde and benzaldehyde-derivative compounds are compounds according to formula II as defined herein-below. They include benzaldehyde and certain benzaldehyde-derivatives whose chemical structure is shown below.

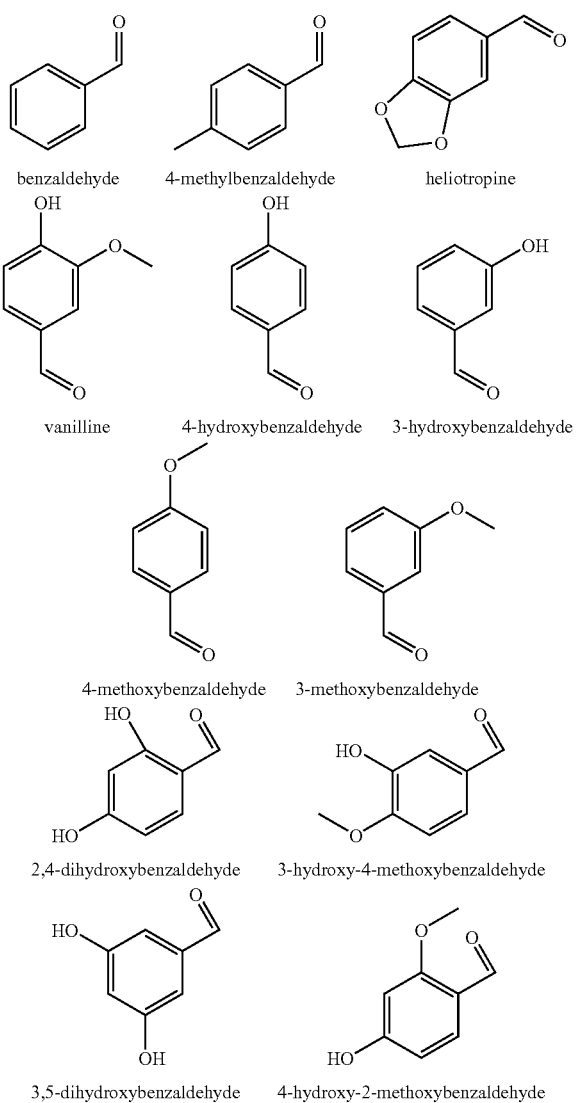

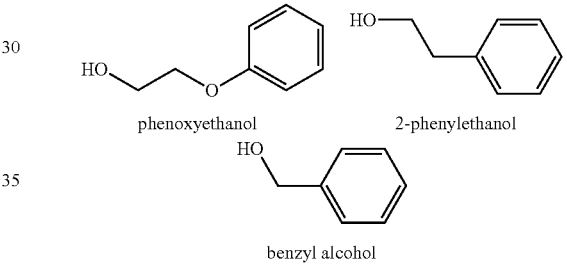

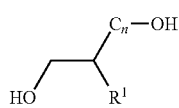

All compounds for use in the invention are commercially available.

Some of these compounds have previously been shown to have a fungistatic effect against various food spoilage molds and yeasts. The antifungal activity of a given antifungal against a given fungal species varies with the food product in which it is used, possibly due to the concentration of lipids or proteins. Fitzgerald et al. report vanillin and various derivatives to have antifungal (fungistatic) activity against a variety of food molds including various *Aspergillus* species (*A. oryzae, A sojae*), *Penicillium* species, and yeast strains when tested in yeast extract peptone dextrose broth. The efficacy against various fungal strains varies. Fungicidal or sporicidal activities were not tested. (J. Agric. Food Chem. 2005, 53, 1769-1775).

Similarly, heliotropin is known to be active as a fungistatic compound in vaporous form when applied to fungi on tobacco leaves, and to have an antifungal and antibacterial effect against some fungi and bacteria in aqueous culture media.

While many substituted benzaldehydes and benzyl alcohols are known to have a germistatic activity against some microorganisms, the germicidal effect, in particular the bactericidal and fungicidal effect, is generally considered to be low, especially when the pH is within the range commonly used in personal care products, which is pH 5 to pH 9. While some compounds are known to be more active under extremely acidic or alkaline conditions, this effect does not extend to the pH range used in personal care products.

That compounds that are fungistatic in certain food stuffs can provide a fungicidal and sporicidal effect in personal care products that often contain lipids and proteins or a high concentration of detergents was completely surprising and could not have been predicted. As can be seen from the examples in this application, an activity or lack of activity of a given test compound in water is not indicative of an activity in a personal care product, for example, a cosmetic cream. In particular, an enhancing effect when used in combination with certain known preservatives in personal care products is not predictable.

Optionally, in addition to the preservative compounds a) above, the following known preservative compounds, which also are commonly used in personal care products, may be added:

SUMMARY OF THE INVENTION

In a first aspect, there is provided a personal care product composition comprising a) at least one diol compound according to formula (I)

$$\underset{HO}{\overset{C_n-OH}{\underset{R^1}{\bigtriangleup}}} \quad FI$$

wherein R1 is selected from methyl, and a $C_1$—$R_2$, $C_3$ (propyl), $C_4$ (butyl), and $C_6$ alkane (hexyl), and wherein R2 is 2-ethyl-hexyloxy;

and wherein n is selected from 0, and 1, and wherein when n is 1, then R1 is $C_1$ (methyl), and wherein the diol compound is selected from the group consisting of 1,2-pentanediol, 1,2-hexanediol, 1,2-octanediol, 2-methyl-1,3-propandiol, and 3-(2-ethyl-hexyloxy)-1,2-propandiol, and wherein the at least one compound according to formula I is present in a total concentration of 0.1% to 2% (w/w); and b) at least one compound according to formula II

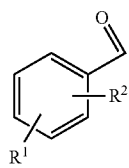

wherein R1 and R2 are selected from H, methyl, hydroxy, methoxy, or R1 together with R2 forms a 3,4-methylendioxy substituent, and
wherein if R1 is H then R2 is selected from H, methyl, hydroxy, and methoxy, and
wherein if R2 is hydroxy, then R1 is selected from H, hydroxy, and methoxy, and
wherein said compound is selected from the group consisting of benzaldehyde, 4-methylbenzaldehyde, heliotropine, vanilline, 4-hydroxybenzaldehyde, 3-hydroxybenzaldehyde, 4-methoxybenzaldehyde and 3-methoxybenzaldehyde, 2,4-dihydroxybenzaldehyde, 3-hydroxy-4-methoxybenzaldehyde, 3,5-dihydroxybenzaldehyde, and 4-hydroxy-2-methoxybenzaldehyde; and
wherein the at least one compound according to formula II is present in a total concentration of 0.05 to 0.5% (w/w);
c) optionally at least one compound selected from the group consisting of phenoxyethanol, 2-phenylethanol, and benzylalcohol, in a total concentration of 0.05 to 0.3% (w/w);
and a cosmetically-acceptable base,
with the proviso that the composition is free from a bactericidally-, fungicidally-, sporicidally-effective or preservative concentration of compounds selected from the group consisting of:
formaldehyde; a formaldehyde donor compound including diazolidinyl urea, imidazolidinyl urea, and DMDM Hydantoin;
parabens selected from the group consisting of methyl-paraben, ethyl-paraben, propyl-paraben, isopropyl-paraben, butyl-paraben, isobutyl-paraben, and benzyl-paraben.
a halogenated compound including 2,4-dichlorobenzyl-alcohol, 4-chloro-3,5-dimethyl-phenol, 2-bromo-2-nitropropane-1,3-diol, and iodopropynyl butyl carbamate;
and a fungicide selected from quaternium-15 (CAS 51229-78-8), methyl-chloroisothiazolinone, and methylisothiazolinone.

In another aspect there is provided a personal care product composition as hereinabove described wherein the at least one compound a) is present in a concentration selected from 0.1 to 1%, and 0.15 to 0.5% (w/w);
a personal care product composition as described above wherein the at least one compound b) is present in a concentration selected from 0.075 to 0.3%, and 0.1 to 0.2% (w/w),
a personal care product composition as hereinabove described wherein the at least one compound a) is present in a concentration of 0.1 to 1% (w/w), and wherein the at least one compound b) is present in a concentration selected from 0.075 to 0.3%, and 0.1 to 0.2% (w/w),
and a personal care product composition as hereinabove described wherein the at least one compound a) is present in a concentration of 0.15 to 0.5% (w/w), and wherein the at least one compound b) is present in a concentration selected from 0.075 to 0.3%, and 0.1 to 0.2% (w/w), In a still further aspect, there are provided personal care product compositions as hereinabove described wherein at least one compound c) as hereinabove described is present in a concentration selected from 0.05% to 0.3% (w/w), 0.075 to 0.25, and 0.15 to 0.2%.

In a yet further aspect there is provided a personal care product composition as hereinabove described selected from compositions for personal care products applied to and left on the skin or scalp including creams, salves, lotions, and ointments for hand, face or body, perfumes, eau de Cologne, eau de toilet, deodorants, antiperspirants, and products applied to and rinsed off the skin or scalp including soaps, liquid soaps, shower gels, and shampoos.

In another aspect there is provided a personal care product comprising a personal care product composition as hereinabove described, in an application form selected from stick, roll-ons, spray, pump-spray, aerosol, soap bar, powder, solution, gel, cream, balm and lotion.

In still another aspect there is provided a personal care product or composition therefor as hereinabove described wherein the personal care product composition comprises lipids.

In a particular embodiment, the above lipid-comprising personal care product composition is provided in form of an emulsion.

In yet another aspect, there is provided a personal care product or composition therefor as hereinabove described wherein the pH is 5 to 9.

In a further aspect there is provided the use of at least one compound a) as hereinabove defined and at least one compound b), and optionally at least one compound c) as hereinabove defined, for the preparation of a preserved personal care product composition, or a preserved personal care product.

In another aspect there is provided a method of forming a preserved personal care product composition which is sufficiently bactericidal to have a reduction factor for *Pseudomonas aeruginosa* and *Staphylococcus aureus* of at least 1000 per 7 days, and is sufficiently sporicidal to have a reduction factor of 100 per 7 days for *Aspergillus niger*, by admixing an effective amount of the at least one compound a) and the at least one compound b), and optionally at least one compound c) as hereinabove defined to a personal care product base, forming a personal care product composition with the proviso as hereinabove defined.

In another aspect there is provided a method of making a preserved personal care product by providing the personal care product composition formed as hereinabove described in a suitable personal care product application form that includes sticks, roll-ons, sprays, pump-sprays, aerosols, soap bars, powders, solutions, gels, creams, balms and lotions.

Bases for personal care products are well known in the art and the resulting personal care product will usually have a pH of pH5 to pH9 (for example, slightly acidic for products applied to and left on the skin, slightly alkaline for soap products). It is also possible to employ an existing personal care product composition and simply add a) and b) and optionally c) in the concentrations hereinabove defined and mix thoroughly.

The exact concentration of compounds under a) and b) and optionally c) that is employed in a composition will depend upon the nature of the product and the preservative effect and length to be achieved, in particular the bactericidal, fungicidal and sporicidal activity.

A useful concentration for the diol compound(s) a) is, for example, 0.1 to 2%, 0.1 to 1% or 0.15 to 0.5% (w/w).

A useful concentration for the preservative enhancer compound(s) b) is, for example, 0.05 to 5%, 0.075 to 0.3%, or 0.1 to 0.2% (w/w).

A useful concentration for optional mild preservative compound(s) c) is, for example 0.05 to 0.3%, 0.075 to 0.25%, or 0.15 to 0.2% (w/w).

In the given concentrations, the diol compound(s) a) and the preservative enhancer b) generally provide a sufficient bactericidal, fungicidal and sporicidal activity in a wide range of personal care product compositions. Optional mild preservative enhancer compounds(s) c) adds to the preservative effect when used in the concentrations indicated.

In particular, a sufficient bactericidal activity is attained when the reduction factor is 1000 per 7 days.

A sufficient sporicidal activity is attained when the reduction factor is 100 per 7 days. A sufficient sporicidal activity is strongly indicative of a sufficient fungicidal activity. Fungicidal activity may easily be tested on yeast strains, using a mix of three *Candida* strains as described in example 4. A sufficient fungicidal activity is reached when the reduction factor is 100 per 7 days.

The reduction factor is determined by growing a suitable test organism (*Aspergillus niger* for fungi, *Pseudomonas aeruginosa* for gram-negative bacteria and *Staphylococcus aureus* for gram-positive bacteria) on a suitable culture medium on agar plates, harvesting and adding to a personal care product composition in a density of $3 \times 10^5$ organism/ml and counting the plated organisms in the probe and a negative control. The count of the negative control is divided by the count of the probe and thereby the reduction factor is determined (compare example 1).

Preservative enhancers of particular interest are 4-hydroxybenzaldehyde and 3-hydroxybenzaldehyde, for their surprisingly good activity.

The addition of hydroxy groups to benzaldehyde and derivatives was previously shown not to provide a fungicidal effect on *A. niger*.

Fitzgerald et al (who looked at fungistatic effects only, and only of certain food-relevant fungi excluding *A. niger*), found that the removal of hydroxy groups from 4-hydroxybenzaldehyde resulted in a slight improvement of fungistatic activity against certain food molds, and the only position beneficial for antifungal (fungistatic) activity was the 2-OH position within the benzene ring of benzaldehyde (J. Agric. Food Chem. 2005, 53, 1769-1775).

Furthermore the abovementioned compounds have only a low fragrance intensity. While highly fragrant compounds such as vanillin are restricted in their usefulness in personal care products depending on the fragrance note to be achieved (which may not be compatible), the abovementioned compounds can be combined with almost any personal care product without significantly altering the fragrance profile.

Personal care product compositions are used to form a personal care product in an appropriate application form and packaging, as is well-known in the art.

Personal care products and compositions to form them as described herein are used for the purpose of cleansing, conditioning, grooming, beautifying, promoting attractiveness, or otherwise enhancing or altering the appearance of the human body and are applied to the human skin or scalp.

These include products applied to and left on the skin or scalp, for example creams, salves, lotions, and ointments for hand, face or body, perfumes, eau de Cologne, eau de toilet, deodorants, antiperspirants, and products applied but rinsed off such as soaps, liquid soaps, shower gels, shampoos.

These products can, for example, take various forms of application, for example sticks, roll-ons, sprays, pump-sprays, aerosols, soap bars, powders, solutions, gels, creams, balms and lotions.

Many personal care products will be formulated as an emulsion or other lipid-containing products and these form a particular aspect. Lipids are often included for example into washing formulations including liquid soaps or washing lotions to provide an oil replenishing effect. Preservative-enhancing compounds as hereinabove defined allow the formulation of preserved emulsions or formulations comprising lipids and/or detergents where the activity (the bactericidal, fungicidal and in particular the sporicidal effect) is not lost due to the presence of the lipid base and/or detergents or surfactants.

Depending on the nature of the personal care product, compounds of the present invention may also be combined with art-recognised quantities of other excipients commonly employed in these products; useful selections may be found in <<CTFA Cosmetic Ingredient Handbook>>, J. M. Nikitakis (ed.), 1st ed., The Cosmetic, Toiletry and Fragrance Association, Inc., Washington, 1988, which is hereby incorporated by reference.

In general, excipients may, for example, include colorants, fragrances, solvents, surfactants, colorants, opacifiers, buffers, antioxidants, vitamins, emulsifiers, UV absorbers, silicones and the like. All products can also be buffered to the desired pH using commonly-available excipients in a known manner.

There now follows a series of non-limiting examples that serve to illustrate the invention.

While the personal care product compositions, products, and related methods have been described above in connection with certain illustrative embodiments, it is to be understood that other similar embodiments may be used or modifications and additions may be made to the described embodiments for performing the same function. Further, all embodiments disclosed are not necessarily in the alternative, as various embodiments may be combined to provide the desired characteristics. Variations can be made by one having ordinary skill in the art without departing from the spirit and scope of the disclosure. Therefore, the compositions, products and methods should not be limited to any single embodiment, but rather construed in breadth and scope in accordance with the recitation of the attached claims.

EXAMPLES

Example 1

Sporicidal Effect of Test Compounds in Water

*Aspergillus niger* ATCC 16404 spores are added to water to obtain a density of $3 \times 10^5$ spores/ml.

In order to prepare the spores, the test strain is grown for 5 days on potato dextrose agar at room temperature. The spores are harvested with a solution containing 0.1% Tween 80, peptone 0.1% and NaCl 0.85% and the spore concentration is adjusted to the density indicated above.

Test compounds are dissolved in dipropyleneglycol to a concentration of 20%.

These stock solutions are added to 10 ml aliquots of the spore suspension to obtain a final concentration of the test compounds of 0.1%. The sporicidal effect is shown by a reduction of spore counts after 7 days.

The reduction factor is determined as follows. Aliquots of the above prepared suspension of microorganisms (here: spore suspension prepared as described above) are plated on a suitable agar medium (see above) and the developing colonies are counted both for samples with test compound and for a negative probe (water). The count of the negative control is divided by the count of the test compound and thereby the reduction factor is determined. A negative control (water) accordingly has a reduction factor of 1 (no effect on the microorganism).

TABLE 1

Sporicidal effect of test compounds in water

| Test compound | 0.1% test compound | |
|---|---|---|
| | Spores/ml | Reduction factor |
| Negative control (water) | $2.5 \times 10^5$ | 1 |
| Cuminic alcohol | $>1.2 \times 10^5$ | <2 |
| Mefranal (3-methyl-5-phenylpentanal) | $4 \times 10^3$ | 63 |
| 9-decenol | $1.1 \times 10^4$ | 23 |
| 4-hydroxybenzaldehyde | $>1.2 \times 10^5$ | <2 |
| 4-methoxy-benzaldehyde | $4.68 \times 10^4$ | 5 | n.d. not determined

No significant reduction of spore counts is achieved with 4-hydroxybenzaldehyde and 4-methoxybenzaldehyde.

Mefranal, and 9-decenol show a significant sporicidal effect.

Example 2

Activity Against Bacteria, Yeast and Mold Spores in a Cosmetic Cream

A preservative-free oil-in-water emulsion skin cream is used. Test samples of cream are made up to contain different amounts of diol compounds and/or benzaldehyde derivatives.

The diol compound and the benzaldehyde derivatives is added to an aliquot of 10 g of the cream in 50 ml tubes in a concentration as shown in the table below. After addition of the preservative/preservative enhancer, the cream is thoroughly mixed to achieve a homogeneous distribution. The cream is then stored for 1-3 days to equilibrate at room temperature (in order to achieve a homogenous partitioning of compounds between oil and water phase).

For testing of sporicidal effect, to each sample 100 µl of a spore suspension of *Aspergillus niger* ATCC 16404 containing $3 \times 10^7$ spores/ml (prepared as described in example 1) is added.

After regular test intervals, samples of 1 g cream are removed and added to 20 ml of a neutralizer solution containing 0.2% lecithin, 2% Tween 80 and 0.5% NaCl. These dilutions are vigorously shaken for 10 min until the cream is dissolved, and then aliquots of this solution are spread plated on potato dextrose agar containing 0.2% Tween 80. After 48 h to 72 h the number of surviving colony forming units (and therefore surviving spores) are counted.

For testing of the bactericidal effect, as test organisms *Staphylococcus aureus* (DSMZ 799) and *Pseudomonas aeruginosa* (ATCC 15442) are used. The strains are grown overnight in Mueller-Hinton broth and adjusted to a cell density of $1 \times 10^8$ cfu (colony forming units) per ml.

The two bacterial strains are mixed in a ratio of 1:1 and 100 µl of this mixed inoculum is added to 10 ml aliquots of the cosmetic cream supplemented with test compounds as described above in the concentration as indicated in the table below.

The resulting mixtures are incubated at room temperature and at the regular intervals samples are removed, suspended in neutralizer solution and diluted as described above.

Aliquots of these suspended and diluted samples are plated on tryptic soy agar supplemented with 0.5% Tween 80 and then incubated for 24 h at 37° C. Surviving bacteria are counted.

For testing of fungicidal activity, the same procedure as described above except for the following is performed with a mixture of the three yeast strains *Candida albicans* ATCC 10231, *Candida guilliermondii* ATCC 6260 and *Candida parapsilosis* ATCC 22019 that replace the bacterial strains.

The yeast strains are grown in Sabouraud liquid medium, washed and suspended in saline and adjusted to $5 \times 10^7$ cfu (colony forming units) per ml. The Inoculum of the three strains is then pooled in a ratio of 1:1:1. For determining the reduction factor by counting of the colonies formed, the samples inoculated with the yeast strains are spread plated on potato dextrose, incubated until colonies have formed and counted.

The results for the Test organism *A. niger* are shown in the table below.

TABLE 2

Activity of test compositions against bacteria, yeasts (vegetative form), and fungal spores

| concentration 4-hydroxybenzaldehyde | Diol compounds | reduction factor 7d fungal spores |
|---|---|---|
| 0% | 0% | 1 |
| 0.1% | 0% | 1 |
| 0% | 1.5% Diol-mixture (1% 1,2-hexanediol, 0.5% 1,2-octanediol) | 10.2 |
| 0.1% | 1.5% Diol-mixture (1% 1,2-hexanediol, 0.5% 1,2-octanediol) | >1016 |

The count of the negative control is divided by the count of the probe and thereby the reduction factor is determined. The negative control with no Diol and no benzaldehyde derivative by definition has a reduction factor of 1. With a benzaldehyde derivative in a concentration 0.1% but no Diol-compound present, the reduction factor is not improved, no sporicidal effect is seen at this concentration.

However, the benzaldehyde derivative at a concentration of 0.1% in combination with 1.5% of a 1,2-hexanediol/1,2-octanediol mixture shows an excellent reduction factor, while the Diol-mixture shows no significant sporicidal activity at this concentration.

Similar results are obtained when 1,2-pentanediol, 2-ethylhexyl-glycerin (=3-(2-ethylhexyloxy)propane-1,2-diol), 1,2-hexanediol, 1,2-octanediol, 2-Methyl-1,3-propanediol or any other combinations thereof are used as the sporicidal Diol component.

Furthermore, similar results are obtained when using benzaldehyde, 4-methylbenzaldehyde, heliotropine, vanilline, 4-hydroxybenzaldehyde, 3-hydroxybenzaldehyde, 4-methoxybenzaldehyde and 3-methoxybenzaldehyde as preservative enhancers in a concentration of 0.1%, or 0.5%. Similar effects are also observed, when testing against bacteria as described above.

Example 2b

Activity Against Bacteria, Yeast and Mold Spores in a Cosmetic Cream b)

The example is performed as described in example 2 except for the following changes:

The preservative-free cosmetic cream for application to the human skin is Cremor basalis (commercially available from Fagron GmbH, Barsbüttel, Germany). The amounts of diol compounds and benzaldehyde derivatives that are added to an aliquot of 10 g of the cream in 50 ml tubes to give a concentration (w/w) of 0.125-4% are as shown in the table below, as are the results obtained.

TABLE 3

Activity of test compositions against *A. niger* spores in a skin cream with different diols alone or in combination with 4-hydroxybenzaldehyde (4-HBA)

| Preservative used | Concentration preservative [%] | Concentration 4-HBA [%] | Reduction factor fungal spores, 7d |
|---|---|---|---|
| No added diol compound (control) | 0 | 0.125 | 5.5 |
| 2-Methyl-1,3-propandiol | 4 | | 25.9 |
| 2-Methyl-1,3-propandiol | 2 | | 3.3 |
| 2-Methyl-1,3-propandiol | 2 | 0.125 | >300 |
| 1,2-Octandiol | 0.25 | | 2.2 |
| 1,2-Octandiol | 0.25 | 0.125 | >300 |
| 3-(2-ethyl-hexyloxy)-1,2-propandiol | 0.5 | | 57.6 |
| 3-(2-ethyl-hexyloxy)-1,2-propandiol | 0.25 | | 3.9 |
| 3-(2-ethyl-hexyloxy)-1,2-propandiol | 0.25 | 0.125 | 391.7 |

2-4% 2-Methyl-1,3-propandiol, 0.25% of 1,2-Octandiol or 0.25% of 3-(2-ethyl-hexyloxy)-1,2-propandiol all were not sufficient to strongly reduce the spore counts, leading to low reduction factor of 3.3 to 25.9

0.125% 4-hydroxybenzaldehyde on its own is insufficient to provide a strong fungal spore reduction as well (reduction factor of 5.5), and even at 0.5% only gives a relatively low reduction factor of 57.6.

However, a combination of 4-hydroxybenzaldehyde with diol-compounds gives highly efficient reduction in fungal spores of well above 100 even at comparatively low concentrations: a combination with 2% 2-methyl-1,3-propandiol shows a reduction factor of >300, and a for the combination with 0.25% 1,2-Octandiol again reaches a reduction factor of >300, and 391.7 for the combination with 3-(2-ethyl-hexyloxy)-1,2-propandiol).

These combinations of 4-hydroxybenzaldehyde with the diols therefore allows to form compositions essentially free of classical preservatives which still provide sufficient reduction of fungal spore counts.

The invention claimed is:

1. A personal care product composition comprising:
   a) at least one diol compound selected from the group consisting of:
      1,2-pentanediol, 1,2-hexanediol, 1,2-octanediol, 2-methyl-1,3-propanediol, and 3-(2-ethyl-hexyloxy)-1,2-propandiol, and wherein the at least one diol compound is present in said composition a total concentration of 0.1% to 2% (w/w); and
   b) 4-hydroxybenzaldehyde present in said composition in a total concentration of 0.05 to 0.5% (w/w);

and a cosmetically-acceptable base, with the proviso that the said composition is free from a bactericidally-, fungicidally-, sporicidally-effective or preservative-effective concentration of compounds selected from the group consisting of:

formaldehyde; a formaldehyde donor compound selected from the group consisting of: diazolidinyl urea, imidazolidinyl urea, and DMDM Hydantoin; parabens selected from the group consisting of: methyl-paraben, ethyl-paraben, propyl-paraben, isopropyl-paraben, butyl-paraben, isobutyl-paraben, and benzyl-paraben, a halogenated compound selected from the group consisting of: 2,4-dichlorobenzyl-alcohol, 4-chloro-3,5-dimethyl-phenol, 2-bromo-2-nitropropane-1,3-diol, and iodopropynyl butyl carbamate;

and a fungicide selected from the group consisting of:
   quaternium-15 (CAS 51229-78-8), methyl-chloroisothiazolinone, and methylisothiazolinone.

2. The personal care product composition according to claim 1 wherein the at least one diol compound a) is present in a concentration range selected from 0.1 to 0.4%, 0.1 to 0.3%, and 0.15 to 0.25% (w/w).

3. The personal care product composition according to claim 1 wherein the 4-hydroxybenzaldehyde is present in a concentration range selected from 0.075 to 0.3%, and 0.1 to 0.2% (w/w).

4. The personal care product composition according to claim 1 wherein the at least one diol compound a) is present in a concentration of 0.1 to 0.3% (w/w), and wherein the 4-hydroxybenzaldehyde is present in a concentration range selected from 0.075 to 0.3%, and 0.1 to 0.2% (w/w).

5. The personal care product composition according to claim 1 wherein the at least one diol compound a) is present in a concentration of 0.15 to 0.25% (w/w), and wherein the 4-hydroxybenzaldehyde is present in a concentration range selected from 0.075 to 0.3%, and 0.1 to 0.2% (w/w).

6. The personal care product composition according to claim 1 which is a personal care product applied to and left on the skin or scalp or is a personal care product applied to and rinsed off the skin or scalp.

7. The personal care product composition according to claim 1 wherein the personal care product composition comprises lipids.

8. The personal care product composition according to claim 7 wherein the composition is an emulsion.

9. The personal care product composition according to claim 1 having a pH of 5 to 9.

10. The personal care product composition according to claim 6 in the form of a personal care product applied to and left on the skin or scalp selected from: creams, salves, lotions, and ointments for hand, face or body, perfumes, eau de Cologne, eau de toilet, deodorants, and antiperspirants.

11. The personal care product composition according to claim 6 in the form of a personal care product applied to and rinsed off the skin or scalp selected from: soaps, liquid soaps, shower gels, and shampoos.

12. The personal care product composition according to claim 1 which further comprises:
   at least one compound c) selected from the group consisting of: phenoxyethanol, 2-phenoxyethanol, 2-phenylethanol and benzylalcohol, which said at least one compound is present in the said composition in a total concentration of 0.05 to 0.3% (w/w).

13. The personal care product composition according to claim 12 wherein the at least one compound c) is present in a concentration selected from 0.05% to 0.3% (w/w), 0.075 to 0.25, and 0.15 to 0.2%.

14. A personal care product comprising a personal care product composition according to claim 1.

15. A personal care product composition comprising
   a) at least one diol compound selected from the group consisting of: 1,2-pentanediol, 1,2-hexanediol, 1,2-octanediol, 2-methyl-1,3-propanediol, and 3-(2-ethyl-hexyloxy)-1,2-propanediol, and which the at least one diol compound is present in a total concentration of 0.1% to 2% (w/w); and
   b) 4-hydroxybenzaldehyde which is present in a total concentration of 0.05 to 0.5% (w/w);
   c) optionally at least one compound selected from the group consisting of: phenoxyethanol, 2-phenylethanol, and benzylalcohol, which said at least one optional compound is present in a total concentration of 0.05 to 0.3% (w/w);
   and a cosmetically-acceptable base,
   with the proviso that the personal care product composition is free from a bactericidally-, fungicidally-, sporicidally-effective or preservative-effective concentration of compounds selected from the group consisting of:
   formaldehyde;
   formaldehyde donors;
   parabens selected from the group consisting of: methyl-paraben, ethyl-paraben, propyl-paraben, isopropyl-paraben, butyl-paraben, isobutyl-paraben, and benzyl-paraben,
   a bactericidally-, fungicidally-, sporicidally-effective or preservative-effective halogenated compound; and,
   a fungicide selected from the group consisting of: quaternium-15 (CAS 51229-78-8), methyl-chloroisothiazolinone, and methylisothiazolinone.

16. A personal care product composition comprising:
   a cosmetically-acceptable base; and,
   a) 0.1% to 2% (w/w) of at least one diol compound selected from the group consisting of: 1,2-pentanediol, 1,2-hexanediol, 1,2-octanediol, 2-methyl-1,3-propanediol, and 3-(2-ethyl-hexyloxy)-1,2-propanediol; and,
   b) 0.05 to 0.5% (w/w) of at least one compound selected from the group consisting of: 4-hydroxybenzaldehyde;
   c) further, optionally, 0.05 to 0.3% (w/w) of at least one compound selected from the group consisting of: phenoxyethanol, 2-phenylethanol, and benzylalcohol,
   with the proviso that the said composition is free from a bactericidally-, fungicidally-, sporicidally-effective or preservative-effective concentration of compounds selected from the group consisting of:
   formaldehyde;
   formaldehyde donor compounds;
   parabens selected from the group consisting of: methyl-paraben, ethyl-paraben, propyl-paraben, isopropyl-paraben, butyl-paraben, isobutyl-paraben, and benzyl-paraben,
   a bactericidally-, fungicidally-, sporicidally-effective or preservative-effective halogenated compound, and
   a fungicide selected from the group consisting of quaternium-15 (CAS 51229-78-8), methyl-chloroisothiazolinone, and methylisothiazolinone.

17. A personal care product comprising the composition of claim 1, present in an application form selected from: stick, roll-on, spray, pump-spray, aerosol, soap bar, powder, solution, gel, cream, balm and lotion.

18. The method of preparing a preserved personal care product composition, comprising the step of:
   forming a personal care product composition according to claim 1.

19. The method according to claim 18, characterized in that the preserved personal care product composition is sufficiently bactericidal to have exhibit a reduction factor for *Pseudomonas aeruginosa* and *Staphylococcus aureus* of at least 1000 per 7 days, and which is sufficiently sporicidal to exhibit a reduction factor of at least 100 per 7 days for *Aspergillus niger*.

20. A method of preparing a preserved personal care product comprising the steps of:
   providing the personal care product composition formed according to claim 18 into a personal care product application form selected from: sticks, roll-ons, sprays, pump-sprays, aerosols, soap bars, powders, solutions, gels, creams, balms and lotions.

* * * * *